US012806229B2

(12) United States Patent
López Pedrosa et al.

(10) Patent No.: US 12,806,229 B2
(45) Date of Patent: Nov. 24, 2026

(54) METHODS OF INCREASING HEIGHT AND PROMOTING LINEAR BONE GROWTH

(71) Applicant: ABBOTT LABORATORIES, Abbott Park, IL (US)

(72) Inventors: José María López Pedrosa, Cenes de la Vega (ES); Ricardo Rueda Cabrera, Granada (ES); Jorge García Martínez, Armilla (ES)

(73) Assignee: ABBOTT LABORATORIES, Abbott Park, IL (US)

( * ) Notice: Subject to any disclaimer, the term of this patent is extended or adjusted under 35 U.S.C. 154(b) by 538 days.

(21) Appl. No.: 18/253,073

(22) PCT Filed: Nov. 17, 2021

(86) PCT No.: PCT/US2021/059599
§ 371 (c)(1),
(2) Date: May 16, 2023

(87) PCT Pub. No.: WO2022/108956
PCT Pub. Date: May 27, 2022

(65) Prior Publication Data

US 2024/0009245 A1 Jan. 11, 2024

(30) Foreign Application Priority Data

Nov. 18, 2020 (EP) .................................... 20383006

(51) Int. Cl.

| | |
|---|---|
| ***A61K 35/20*** | (2006.01) |
| ***A23C 9/142*** | (2006.01) |
| ***A23L 33/00*** | (2016.01) |
| ***A23L 33/10*** | (2016.01) |
| ***A61K 9/127*** | (2025.01) |
| ***A61K 9/1276*** | (2025.01) |
| ***A61K 47/18*** | (2017.01) |
| ***A61K 47/42*** | (2017.01) |
| ***A61P 19/00*** | (2006.01) |
| ***B01D 61/14*** | (2006.01) |

(52) U.S. Cl.
CPC ............ *A61K 35/20* (2013.01); *A23C 9/1425* (2013.01); *A23L 33/10* (2016.08); *A23L 33/40* (2016.08); *A61K 9/1276* (2013.01); *A61K 47/183* (2013.01); *A61K 47/42* (2013.01); *A61P 19/00* (2018.01); *B01D 61/145* (2013.01); *B01D 61/147* (2013.01); *B01D 61/149* (2022.08); *A23C 2210/206* (2013.01); *B01D 2315/16* (2013.01)

(58) Field of Classification Search
CPC .... A61K 35/20; A61K 9/1276; A61K 47/183; A61K 47/42; A23L 33/10; A23L 33/40; A61P 19/00; B01D 61/149; B01D 61/145; B01D 61/147; B01D 2315/16; A23C 9/1425; A23C 2210/206
See application file for complete search history.

(56) References Cited

U.S. PATENT DOCUMENTS

| | | | |
|---|---|---|---|
| 10,543,259 | B2 | 1/2020 | Dauber et al. |
| 2017/0296590 | A1 | 10/2017 | Cho et al. |

FOREIGN PATENT DOCUMENTS

| | | | | |
|---|---|---|---|---|
| CN | 107296098 A | 10/2017 | | |
| CN | 108478600 A | 9/2018 | | |
| CN | 110151726 A | 8/2019 | | |
| KR | 10-2018-0092348 A | 8/2018 | | |
| KR | 10-2035273 B1 | 10/2019 | | |
| WO | WO-0178530 A2 * | 10/2001 | ............. | A61P 43/00 |
| WO | 2019/104169 A1 | 5/2019 | | |
| WO | 2019/209061 A1 | 10/2019 | | |
| WO | 2020/028439 A1 | 2/2020 | | |

OTHER PUBLICATIONS

M.C. Oliviera, et al. "Milk-Derived Nanoparticle Fraction Promotes the Formation of Small Osteoclasts but Reduces Bone Resorption," J. Cell. Physiol. 232: 225-233, 2017. (Year: 2017).*
Oliveira, et al. "Milk-Derived Nanoparticle Fraction Promotes the Formation of Small Osteoclasts but Reduces Bone Resorption," J. Cell. Physiol. 2017 232: 225-233. (Year: 2017).*
Ely, et al. "Structure and Functions of Lactoferrin as Ingredient in Infant Formulas," Journal of Food Research; vol. 2, No. 4; 2013, 25-36. (Year: 2013).*
Hong et al. "Isolation of biologically active and morphologically intact exosomes from plasma of patients with cancer," J. Extracellular Vesicles, 2016, 5:29289, p. 1-11. (Year: 2016).*
Blicharski, et al. "A metabolite of leucine (B-hydroxy-B-methylbutyrate) given to sows during pregnancy alters bone development of their newborn offspring by hormonal modulation," PLoS ONE 12(6): e0179693, 2017, 1-25. (Year: 2017).*
Givens, D.I., Milk Symposium review: The importance of milk and dairy foods in the diets of infants, adolescents, pregnant women, adults, and the elderly*, J. Dairy Sci., vol. 103, No. 11, pp. 9681-9699 (Oct. 14, 2020).

(Continued)

*Primary Examiner* — Michael P Cohen
(74) *Attorney, Agent, or Firm* — McAndrews, Held & Malloy, Ltd.

(57) ABSTRACT

A method of increasing height in a pediatric subject comprises enterally administering an exosome-enriched product comprising intact bovine milk-derived exosomes to the pediatric subject in need thereof. A method of promoting linear bone growth in a pediatric subject comprises enterally administering an exosome-enriched product comprising intact bovine milk-derived exosomes to the pediatric subject in need thereof. A method of obtaining an exosome-enriched product from cheese whey comprises subjecting the cheese whey to microfiltration (MF), ultrafiltration (UF), and diafiltration (DF) steps, wherein the MF, UF, and DF steps employ, successively, membranes with cut off values which gradually decrease in size with each filtration step, wherein the cheese whey is sweet cheese whey and has a pH from about 6.0 to about 6.5.

20 Claims, 9 Drawing Sheets

(56) References Cited

OTHER PUBLICATIONS

Go, Gyeongyun et al., Bovine milk extracellular vesicles induce the proliferation and differentiation of osteoblasts and promote osteogenesis in rats, J Food Biochem, vol. 45, No. 4, pp. 1-11 (Apr. 22, 2021).
Jee, Youn Hee et al., The Biology of Stature, Journal of Pediatrics, vol. 173, pp. 32-38 (Mar. 26, 2016).
Leiferman, Amy et al., A diet defined by its content of bovine milk exosomes and their RNA cargos has moderate effects on gene expression, amino acid profiles and grip strength in skeletal muscle in C57BL/6 mice, The Journal of Nutritional Biochemistry, vol. 59, pp. 123-128 (Jun. 12, 2018).
Yun, B. et al., Short communication: Dietary bovine milk-derived exosomes improve bone health in an osteoporosis-induced mouse model, Journal of Dairy Science, vol. 103, No. 9, pp. 7752-7760 (Sep. 1, 2020).
International Search Report, PCT/US2021/059599, dated Apr. 8, 2022, 10 pages.

* cited by examiner

METHODS OF INCREASING HEIGHT AND PROMOTING LINEAR BONE GROWTH

The present application is a National Phase Entry of International Application No. PCT/US2021/059599, filed on Nov. 17, 2021, which claims the benefit of European Patent Application No. EP 20383006.2, filed Nov. 18, 2020, each of which is hereby incorporated by reference in its entirety.

FIELD OF THE INVENTION

The present invention relates to a method of increasing height in a pediatric subject, as well as a method of promoting linear bone growth in a pediatric subject, by administering an exosome-enriched product comprising intact bovine milk-derived exosomes. The present invention also relates to method of obtaining a exosome-enriched product from cheese whey by subjecting the cheese whey to microfiltration (MF), ultrafiltration (UF), and diafiltration (DF) steps which employ, successively, membranes with cut off values which gradually decrease in size with each filtration step.

BACKGROUND OF THE INVENTION

The skeleton is a dynamic tissue with both structural and metabolic roles. Structurally, the skeleton protects organs against damaging mechanical forces, provides levers to transmit forces between different areas of the body, and anchors muscles. The foundation for lifelong skeletal health is primarily established during the first two decades of life. It has thus been shown that maintaining adequate nutrition during childhood and adolescence is crucial for achieving optimum growth, peak body mass, and bone quality. Further, optimizing bone growth during childhood and adolescence is crucial for preventing osteoporosis and fractures later in life. Borges J L, Brandao C M. Low bone mass in children and adolescents. *Arq Bras Endocrinol Metabol* 2006; 50(4): 775-782.

There are a number of factors that may threaten skeletal health. For example, malnutrition, vitamin D insufficiency, malabsorption, abnormal hormonal balance, increased cytokine production, and medications such as glucocorticoids or chemotherapeutic agents, have the potential to negatively affect bone growth and skeletal health. Gat-Yablonski G, Phillip M. Nutritionally-induced catch-up growth. *Nutrients* 2015; 7(1): 517-551; Lui J C. *The Biology of the First* 1,000 *Days*, vol. Chapter 16: Nutritional Regulation of the Growth Plate. 2017.

Malnutrition in particular has been considered a leading cause of short stature and growth attenuation in children ages 4-7. According to the UNICEF-WHO-The World Bank 2012 joint report, linear growth restriction due to chronic malnutrition affects up to 25% of all children younger than 5 years old worldwide. In developing countries, the situation is even worse, with an average of 33% of all children younger than 5 years of age suffering from linear growth restriction due to chronic malnutrition. Rakefet Pando M M et al. Bone quality is affected by food restriction and by nutrition-induced catch-up growth. *Journal of Endocrinology*. 2014; 223(3):227-239.

Linear growth of the axial and appendicular skeleton is a complex and tightly regulated process that occurs in specialized structures located at the distal and the proximal ends of the long bones between the epiphysis and the metaphysis. These structures, termed growth plates, are disks of avascular, alymphatic and aneural cartilage. Hunziker E B. Elongation of the Long Bones in Humans by the Growth Plates. *Nestle Nutr Inst Workshop Ser* 2018; 89: 13-23. Linear bone growth occurs rapidly during fetal life and early childhood, but then progressively slows and ceases during adolescence at 10-12 years of age. During childhood, the growth plate matures, its width decreases, and at the end of the puberty disappears with a complete replacement of bone along with cessation of linear growth. Nilsson O, Baron J. Fundamental limits on longitudinal bone growth: growth plate senescence and epiphyseal fusion. *Trends Endocrinol Metab* 2004; 15(8): 370-374.

In a number of places in the body, such as the skull, maxilla, mandible and other flat bones, bone formation is driven by a process called intramembranous ossification. During intramembranous ossification, bones are formed by the direct differentiation of mesenchymal cells into bone-forming osteoblasts. In most other places, however, bones, such as the long bones that make up the appendicular and axial skeleton, are formed by a different process called endochondral ossification. Wuelling M, Vortkamp A. Chondrocyte proliferation and differentiation. *Endocr* Dev 2011; 21: 1-11; 18. Hallett S A, Ono W, Ono N. Growth Plate Chondrocytes: Skeletal Development, Growth and Beyond. *Int J Mol Sci* 2019; 20(23). Endochondral ossification is achieved by the activity of the growth plates and is a complex process that is strictly regulated at both the systemic and local levels. See Gat-Yablonski G et al. For example, the growth hormone-insulin growth factor-1 axis, the sex hormones (estrogen and androgen)-leptin axis and thyroid hormones are potent stimulators of growth plate activity. On the contrary, glucocorticoids, which are commonly used as anti-inflammatory and immunosuppressive drugs, have the potential to lead to decreased linear growth in children. See Lui J C.

Malnutrition can have a negative effect on bone elongation, and thus growth, due to its effect on the regulators of growth plate activity. For instance, fasting may impair the rate of linear bone growth and to reduce the width of the growth plate, and children with insufficient caloric intake or insufficient protein consumption may have significantly lower height than healthy individuals. Heinrichs C, Colli M, Yanovski J A, Laue L, Gerstl N A, Kramer A D et al. Effects of fasting on the growth plate: systemic and local mechanisms. *Endocrinology* 1997; 138(12): 5359-5365; Soliman A T, ElZalabany M M, Salama M, Ansari B M. Serum leptin concentrations during severe protein-energy malnutrition: correlation with growth parameters and endocrine function. *Metabolism* 2000; 49(7): 819-825.

Unfortunately, even if a bone growth inhibiting condition ceases, children with a prior growth deficiency may end up shorter than is expected even after catch up growth, which may lead to a permanent growth deficit. See Lui J C. Further, bone growth and bone quality may be affected by food restriction and by nutrition-induced catch-up growth. See Rakefet Pando M M et al. It is thus important to address any bone growth inhibiting condition as soon as possible in order to prevent permanent growth complications.

In view of the above, there is an urgent need to develop new and accessible technologies that stimulate growth plate activity, especially in children and adolescents with suboptimal nutrition.

Accordingly, a method of increasing height in a pediatric subject and a method of promoting linear bone growth are desirable.

SUMMARY OF THE INVENTION

It is therefore an object of the invention to provide methods which promote linear bone growth and/or increase height in pediatric subjects.

In one embodiment, the invention is directed to a method of increasing height in a pediatric subject comprising enterally administering an exosome-enriched product comprising intact bovine milk-derived exosomes to the pediatric subject in need thereof.

In another embodiment, the invention is directed to a method of promoting linear bone growth in a pediatric subject comprising enterally administering an exosome-enriched product comprising intact bovine milk-derived exosomes to the pediatric subject in need thereof.

In another embodiment, the invention is directed to a method of obtaining an exosome-enriched product from cheese whey comprising subjecting the cheese whey to microfiltration (MF), ultrafiltration (UF), and diafiltration (DF) steps, wherein the MF, UF, and DF steps employ, successively, membranes with cut off values which gradually decrease in size with each filtration step, wherein the cheese whey is sweet cheese whey and has a pH from about 6.0 to about 6.5.

The methods of increasing height and promoting linear bone growth in a pediatric subject are advantageous in that they provide a convenient therapeutic strategy for preventing, reducing and/or treating linear bone growth restriction in children, for example caused by inadequate nutrition and/or treatments with glucocorticoids or chemotherapeutic agents. These and additional objects and advantages of the invention will be more fully apparent in view of the following detailed description.

BRIEF DESCRIPTION OF THE DRAWINGS

The drawings are illustrative of certain embodiments of the invention and exemplary in nature and are not intended to limit the invention defined by the claims, wherein:

DETAILED DESCRIPTION

Figure 1:
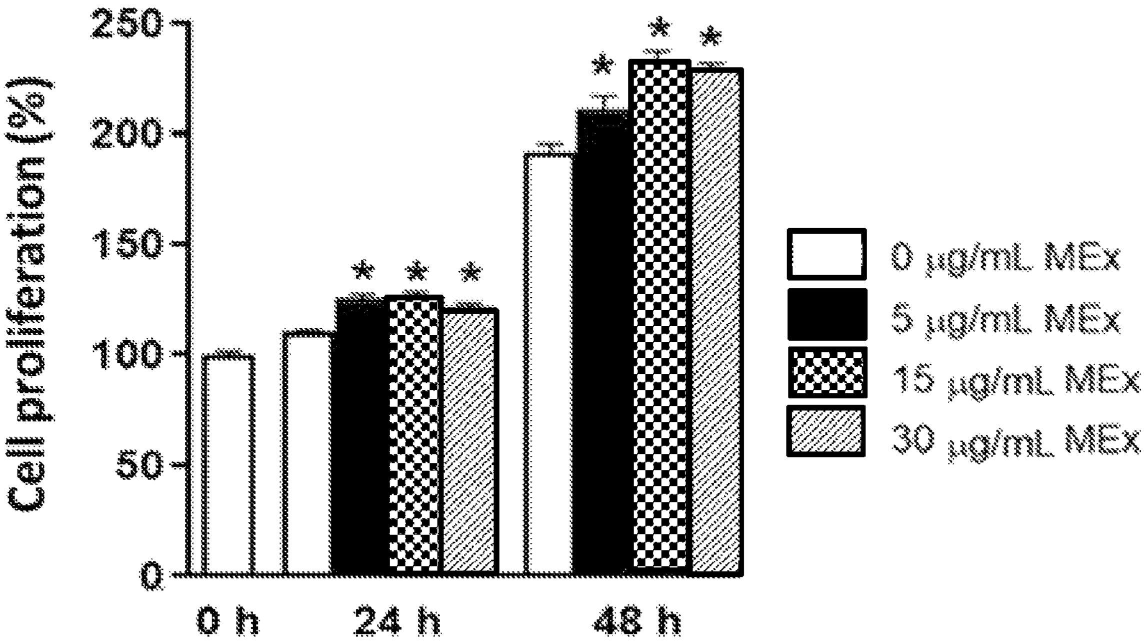
FIG. 1 illustrates chondrocyte viability and proliferation of 028/12 human chondrocyte cells incubated with increasing amounts of an exosome-enriched product containing intact bovine milk-derived exosomes, as described in Example 2.

Specific embodiments of the invention are described herein. The invention can, however, be embodied in different forms and should not be construed as limited to the embodiments set forth herein. Rather, these embodiments are provided to illustrate more specific features of certain embodiments of the invention to those skilled in the art.

The terminology as set forth herein is for description of the embodiments only and should not be construed as limiting the disclosure as a whole. All references to singular characteristics or limitations of the present disclosure shall include the corresponding plural characteristic or limitation, and vice versa, unless otherwise specified or clearly implied to the contrary by the context in which the reference is made. Unless otherwise specified, "a," "an," "the," and "at least one" are used interchangeably. Furthermore, as used in the description and the appended claims, the singular forms "a," "an," and "the" are inclusive of their plural forms, unless the context clearly indicates otherwise.

To the extent that the term "includes" or "including" is used in the description or the claims, it is intended to be inclusive of additional elements or steps, in a manner similar to the term "comprising" as that term is interpreted when employed as a transitional word in a claim. Furthermore, to the extent that the term "or" is employed (e.g., A or B), it is intended to mean "A or B or both." When the "only A or B but not both" is intended, then the term "only A or B but not both" is employed. Thus, use of the term "or" herein is the inclusive, and not the exclusive use. When the term "and" as well as "or" are used together, as in "A and/or B" this indicates A or B as well as A and B.

All ranges and parameters, including but not limited to percentages, parts, and ratios disclosed herein are understood to encompass any and all sub-ranges subsumed therein, and every number between the endpoints. For example, a stated range of "1 to 10" should be considered to include any and all sub-ranges beginning with a minimum value of 1 or more and ending with a maximum value of 10 or less (e.g., 1 to 6.1, or 2.3 to 9.4), and to each integer (1, 2, 3, 4, 5, 6, 7, 8, 9, and 10) contained within the range.

Any combination of method or process steps as used herein can be performed in any order, unless otherwise specified or clearly implied to the contrary by the context in which the referenced combination is made.

All percentages are percentages by weight unless otherwise indicated.

The term "adolescence" as used herein, unless otherwise specified, refers to the period between the ages of about 10 years to 19 years, which normally corresponds with the onset of physiologically normal puberty and ends when an adult identity and behavior are accepted.

The term "an exosome-enriched product comprising bovine milk-derived exosomes" as used herein, unless otherwise specified, refers to a product in which exosomes have been substantially separated from other bovine milk components such as lipids, cells, and debris, and are concentrated in an amount higher than that found in bovine milk. The exosomes are small, extracellular vesicles and account for a minor percentage of milk's total content. In specific embodiments, the exosome-enriched product is provided in a liquid form or a powdered form and also contains co-isolated milk solids.

The term "catch-up growth" as used herein, unless otherwise specified, refers to body growth that occurs at a rate greater than normal for age, following a period of growth inhibition. Clinically, catch-up growth has been observed after growth inhibition due to a variety of causes, including malnutrition, and glucocorticoid excess. Local growth inhibition within a single growth plate leads to local catch-up growth, suggesting that the mechanism responsible for catch-up growth resides, at least in part, within the growth plates themselves. Different studies have shown evidence that this local catch-up growth results from delayed growth plate senescence. Growth inhibiting conditions slow senescence, a process characterized by both structural and functional changes in the growth plate, including the decline in the chondrocyte proliferation rate, the size of the hypertrophic chondrocyte, and, consequently, the rate of longitudinal bone growth. When the growth-inhibiting condition resolves, the growth plates grow more rapidly than is normal for age, resulting in catch-up growth. Since growth-inhibiting conditions slow aging of the growth plate, after the condition resolves, the growth plates grow more rapidly. The maximum growth potential can be influenced by several environmental factors, including nutritional intervention.

The term "enterally" or "enteral administration" as used herein refers to administration involving the esophagus, stomach, and small and large intestines (i.e., the gastrointestinal tract). Examples of enteral administration include oral, including sublingual, and tube feeding.

The term "intact exosomes" as used herein refers to exosomes in which the vesicle membrane is not ruptured and/or otherwise degraded and the endogenous cargo, i.e., the bioactive agents, therapeutics (e.g. miRNA), and/or other biomolecules which are inherently present in a bovine milk-derived exosome, are retained therein in active form.

The term "pediatric subject" as used herein refers to an infant, child, or adolescent up to the age of about 21 years old.

As indicated above, the present invention provides methods of increasing height and promoting linear bone growth in pediatric subjects. Without wishing to be bound by any particular theory, the methods of the present invention promote linear bone growth and/or increase height in pediatric subjects by stimulating chondrocyte proliferation within the growth plate via administration of intact bovine milk-derived exosomes to the pediatric subject in need thereof. The present inventors have surprisingly discovered that intact bovine milk-derived milk exosomes significantly enhance chondrocyte viability and proliferation capacity. As discussed above, chondrocyte proliferation is crucial for bone growth and represents a novel approach to prevent, reduce or treat linear bone growth restriction, for example caused by inadequate nutrition and/or treatments with anti-inflammatory drugs (i.e. glucocorticoids) or chemotherapeutic agents in children.

In one embodiment, the invention is directed to a method of increasing height in a pediatric subject comprising enterally administering an exosome-enriched product comprising intact bovine milk-derived exosomes to the pediatric subject in need thereof.

In another embodiment, the invention is directed to a method of promoting linear bone growth in a pediatric subject comprising enterally administering an exosome-enriched product comprising intact bovine milk-derived exosomes to the pediatric subject in need thereof.

In a specific embodiment of the invention, the dosage of the exosome-enriched product comprising the intact bovine milk-derived exosomes is from about 0.01 to about 30 g. More specifically, the dosage of the exosome-enriched product comprising the intact bovine milk-derived exosomes may be from about 0.1 to about 30 g, from about 0.1 to about 15 g, or from about 1 to about 15 g. The exosome-enriched product comprising the intact bovine milk-derived exosomes can be administered to a subject at any of the above dosages from about 1 to about 6 times per day or per week, or from about 1 to about 5 times per day or per week, or from about 1 to about 4 times per day or per week, or from about 1 to about 3 times per day or per week. By way of example, the dosage of the exosome-enriched product comprising the intact bovine milk-derived exosomes may be from about 0.01 to about 30 g/day, from about 0.1 to about 30 g/day, from about 0.1 to about 15 g/day, or from about 1 to about 15 g/day.

In another specific embodiment, the exosome-enriched product comprises at least wt % exosomes. In another specific embodiment, the exosome-enriched product comprises at least about 0.001 wt %, 0.01 wt %, 1 wt %, 5 wt %, 10 wt %, 15 wt %, 20 wt %, 25 wt %, 30 wt %, 35 wt %, 40 wt %, 45 wt %, or 50 wt % exosomes. In a further embodiment, the exosome-enriched product comprises at least about $10^8$ exosomes per gram of the exosome-enriched product as measured by a nanotracking procedure. Briefly, nanoparticle tracking analysis (NTA) can be used to determine exosome diameter and concentration. The principle of NTA is based on the characteristic movement of nanosized particles in solution according to the Brownian motion. The trajectory of the particles in a defined volume is recorded by a camera that is used to capture the scatter light upon illumination of the particles with a laser. The Stokes-Einstein equation is used to determine the size of each tracked particle. In addition to particle size, this technique also allows determination of particle concentration.

In a more specific embodiment, the exosome-enriched product comprises from about $10^8$ to about $10^{14}$ exosomes per gram of the exosome-enriched product. In yet a more specific embodiment, the exosome-enriched product comprises from about $10^9$ to about $10^{13}$ exosomes per gram of the exosome-enriched product. In another specific embodiment, the exosome-enriched product contains at least about a three-fold increase in the number of exosomes, as compared to a raw whey-containing bovine milk fraction. In a more specific embodiment, the exosome-enriched product contains a 3-fold to 50-fold increase in the number of exosomes, as compared to a raw whey-containing bovine milk fraction, for example cheese whey.

In a specific embodiment, at least about 50 wt % of exosomes in the exosome-enriched product are intact. In another specific embodiment, at least about 55, 60, 65, 70, 75, 80, 85, 90, or 95 wt % of the exosomes in the exosome-enriched product are intact.

In another specific embodiment, the pediatric subject is a child at or under the age of about 18 years old, or at or under the age of about 15 years old, or at or under the age of about years old, or at or under the age of about 5 years old, or at or under the age of about 1 year old, or at or under the age of about 6 months old, or at or under the age of about 3 months old. As mentioned above, longitudinal bone growth occurs rapidly during fetal life and early childhood, but then progressively slows and ceases during adolescence. In fact, approximately 90% of adult bone mass is gained during childhood and adolescence. As such, it is important to provide infants, young children, and adolescents with adequate nutrition in order to ensure optimal bone health later in life.

In a specific embodiment, the pediatric subject is suffering from linear bone growth restriction. In another specific embodiment, the linear bone growth restriction is a result of malnutrition, vitamin and/or mineral deficiency, malabsorption, a hormonal imbalance, type-1 diabetes, or a combination of two or more thereof.

In a specific embodiment, the pediatric subject has undergone, is undergoing, or will undergo chemotherapy treatment. In another specific embodiment, the pediatric subject has taken, is taking, or will be taking at least one glucocorticoid and/or immunosuppressive medication The enriched product of intact bovine milk-derived exosomes is typically obtained from a whey fraction of bovine milk. In a specific embodiment, the intact bovine milk-derived exosomes are sourced from a whey-containing bovine milk fraction. By way of example, the whey-containing bovine milk fraction may comprise cheese whey. Generally, the exosomes are obtained from a whey-containing bovine milk fraction using gentle procedures which do not disrupt the exosome vesicle membrane, thereby leaving the exosomes intact and active bioactive agents contained within the exosome structure.

Various methods may be employed to isolate exosomes with care being exercised to avoid disruption of the lipid membrane. Fresh bovine milk, refrigerated bovine milk, thawed frozen bovine milk, or otherwise preserved bovine milk, or any bovine milk fraction containing exosomes, for example, cheese whey, may be employed as a source of exosomes. Isolating the exosomes may comprise performing the isolation immediately upon obtaining milk from a bovine. By way of example, isolating the exosomes may comprise performing the isolation within about 1 day, or about 2 days, or about 3 days, or about 4 days, or about 5 days or about 6 days, or about 7 days from the time of obtaining the milk from a bovine. The exosomes may be isolated within about 10 days, or within about 14 days from the time of obtaining milk from a bovine. Additionally, the bovine milk may be frozen and then thawed for processing for isolating exosomes, with the bovine milk preferably having been frozen within about 1 day, or about 2 days, or about 3 days, or about 4 days, or about 5 days or about 6 days, or about 7 days from the time of obtaining the milk from a bovine. Thawed milk is preferably processed immediately upon thawing. The fresh bovine milk may be subjected to the processing within about 5 days of obtaining the milk from a bovine, or thawed bovine milk which is subjected to processing is thawed from bovine milk that was frozen within about 5 days of obtaining the milk from a bovine.

As mentioned above, a whey-containing bovine milk fraction or, specifically, cheese whey, may serve as a source of exosomes. Cheese whey is the liquid by-product of milk after the formation of curd during the cheese-making or casein manufacturing process. Since cheese whey has already been separated from the casein fraction during the cheese manufacture process, cheese whey has very low casein content. Furthermore, cheese whey advantageously retains more than 50% of milk nutrients, including lactose, fat, proteins, mineral salts, and, surprisingly, a significant number of exosomes that were originally present in the milk in intact form. In addition to these benefits, cheese whey is less expensive than raw milk, and thus using cheese whey as a starting material significantly reduces costs for production of an exosome-enriched product. As such, cheese whey is a novel and promising source for isolating milk exosomes and producing exosome-enriched products.

In a specific embodiment, the cheese whey is obtained by applying an enzyme or enzyme mixture, and more specifically a protease enzyme, for example chymosin, to milk to hydrolyze casein peptide bonds, thus allowing for enzymatic coagulation of casein in the milk. Thus, when the protease enzyme cleaves the protein, it causes the casein in the milk to coagulate and form a gel structure. The casein protein gel network and milk fat then contract together and form curd. The resulting liquid that is separated from the curd is often referred to as sweet whey or cheese whey, typically has a pH from about 6.0 to about 6.5, and comprises whey proteins, lactose, minerals, water, fat and other low level components.

As indicated above, it is important that the enzyme or enzyme mixture is capable of destabilizing the casein protein in the milk fraction by cleaving peptides which stabilize the casein protein in the milk. Therefore, any proteolytic enzyme suitable for this purpose may be used to obtain cheese whey. In a preferred embodiment, however, the cheese whey is provided by adding rennet enzyme to bovine milk, resulting in enzymatic coagulation of casein. Rennet enzyme is commonly used in the cheese making process and comprises a set of enzymes which are produced in the stomachs of ruminant mammals. These enzymes normally include chymosin, pepsin, and lipase. The rennet enzyme mix destabilizes the casein protein in the bovine milk fraction by proteolytically cleaving peptides which stabilize the protein in the milk. As indicated above, the casein in the milk coagulates and contracts with milk fat to form the cheese curd. The remaining liquid, i.e., the sweet cheese whey, comprises whey proteins, lactose, minerals, water, fat, and other low level components.

Figure 9:
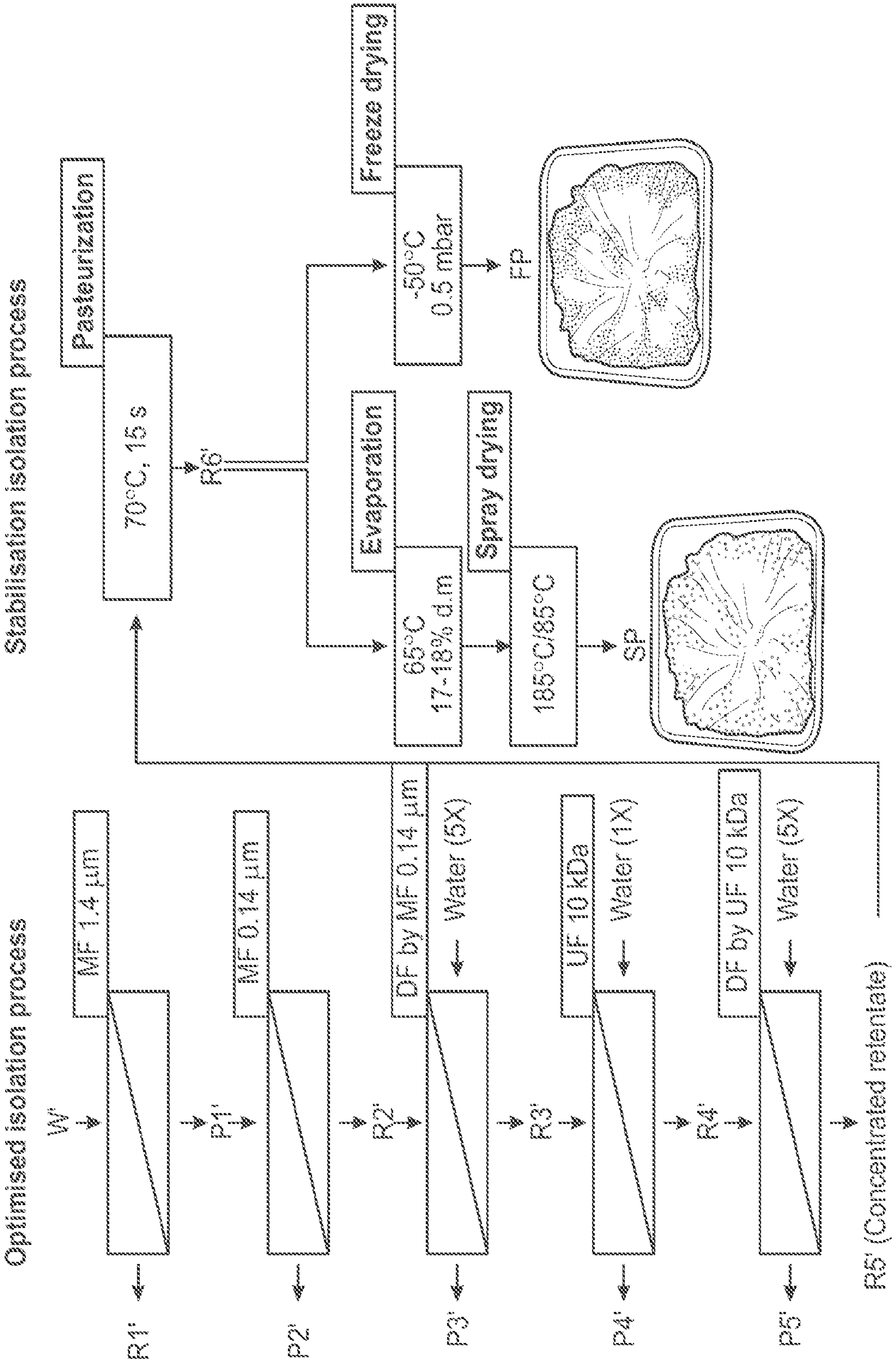
FIG. 9. illustrates a flow diagram of a membrane filtration process coupled to spray-drying or freeze-drying to produce a lactose-free exosome-enriched product from cheese whey, as described in Example 1.

By way of example, a gentle procedure of obtaining an exosome-enriched product containing intact bovine milk-derived exosomes may comprise physical methods and/or chemical methods. In one embodiment, an exosome-enriched product is obtained by cascade membrane filtration. In a specific embodiment, the exosome-enriched product is lactose-free. In a specific embodiment, sweet cheese whey, which may be obtained as described in the preceding paragraph, is processed using tandem multiple ceramic filtration steps. In a specific embodiment, a multiple filtration process employs, successively, membranes with cut offs which gradually decrease in size. In a specific embodiment, the method of processing sweet cheese whey is subjected to microfiltration (MF, ultrafiltration (UF) and diafiltration (DF). In one more specific embodiment, as shown in FIG. 9, the process employs, successively, MF, UF and DF membranes with cut offs of about 1.4 μm, 0.14 μm and 10 kDa, respectively, to provide an exosome-enriched product. For example, a first MF step employs a first membrane with a molecular weight cut off of, for example, about 1.4 μm and yields a first retentate R1 and a first permeate P1. The first permeate P1 is then subjected to a an UF step employing a second membrane with a molecular weight cut off of, for example, about 0.14 μm, which yields a second retentate R2 and second permeate P2. The second retentate R2 may be resuspended in water and again passed through the second membrane to remove additional lactose, minerals and the like, if desired. For example, in one embodiment, about 5 volumes of water may be added to one volume of the second retentate R2 and the resulting suspension is then passed through the 0.14 μm MF membrane. The resulting third retentate R3 is then subjected to a DF step using a 10 kDa membrane. In a specific embodiment, the third retentate is first diluted with an approximately equal volume of water and diafiltered to obtain a fourth retentate R4, and then the fourth retentate R4 is again diluted with water, for example with a volume of water five times that of the fourth retentate R4 and then diafiltered to yield a concentrated retentate R5. This exosome-enriched product may be used in the form of the concentrated retentate R5, or the concentrated retentate R5 may be further processed.

In a specific embodiment, the exosome-enriched product resulting from successive filtration steps may be pasteurized to provide storage stability. For example, the exosome-enriched product may be heated, for example, at about 70° C. for about 15 seconds, to ensure microbiological stability in order to yield a pasteurized fraction, R6. Other pasteurization conditions will be apparent to those skilled in the art and may be employed.

With or without pasteurization, the exosome-enriched product may be used as is or subjected to additional processing steps to provide a desired physical form. In one embodiment, the exosome-enriched product, optionally pasteurized, may be converted to a powder form. In more specific embodiments, the exosome-enriched product can be spray-dried, freeze dried, or otherwise converted to powder form. In one specific embodiment, the exosome-enriched product may be spray dried, for example, at 185° C./85° C., to obtain an exosome-enriched product in the form of a spray-dried powder (SP). Prior to spray drying, the exosome-enriched product may be subjected to an optional evaporation step to increase the solids content of the product and therefore reduce the time and/or energy demand for the spray drying process. Other spray drying conditions will be apparent to those skilled in the art and may be employed. Alternatively, the exosome-enriched product may be freeze-dried, for example at −50° C. and 0.5 mbar vacuum to obtain an exosome-enriched freeze-dried powder (FP). Other freeze drying conditions will be apparent to those skilled in the art and may be employed.

In a specific embodiment, the exosome-enriched product comprising the intact bovine milk-derived exosomes are administered to the pediatric subject orally.

In a specific embodiment, the exosome-enriched product is administered in the form of an exosome-enriched powder. In another specific embodiment, the exosome-enriched product is administered in the form of an exosome-enriched liquid. The exosome enriched product can be administered to the pediatric subject in either form.

In another specific embodiment, the exosome-enriched product comprising intact bovine milk-derived exosomes is administered to the pediatric subject in a nutritional composition. The nutritional composition may be in liquid form or powder form and comprises protein, carbohydrate, and/or fat.

In another specific embodiment, the nutritional composition comprises about 0.001 to about 30 wt %, about 0.001 to about 10 wt %, about 0.001 to about 5 wt %, about 0.001 to about 1 wt %, about 0.01 to about 30 wt %, about 0.01 to about 10 wt %, about 0.01 to about 5 wt %, about 0.01 to about 1 wt %, about 0.1 to about 30 wt %, about 0.1 to about 10 wt %, about 0.1 to about 5 wt %, about 0.1 to about 1 wt %, about 1 to about 30 wt %, about 1 to about 10 wt %, or about 1 to about 5 wt % of the exosome-enriched product comprising the intact bovine milk-derived exosomes, based on the weight of the nutritional composition. In a specific embodiment, the nutritional composition comprises from about 0.001 to about 10 wt % of the I exosome-enriched product comprising the intact bovine milk-derived exosomes, based on the weight of the nutritional composition.

In additional embodiments, the nutritional composition is a liquid composition and comprises about 0.001 to about 10 wt %, about 0.001 to about 5 wt %, about 0.001 to about 1 wt %, about 0.01 to about 5 wt %, about 0.01 to about 1 wt %, about 0.1 to about 5 wt %, about to about 1 wt %, or about 1 to about 5 wt % of the exosome-enriched product comprising the intact bovine milk-derived exosomes, based on the weight of the liquid nutritional composition. In other embodiments, the nutritional composition is a powdered composition and comprises about 0.01 to about 30 wt %, about 0.01 to about 20 wt %, about 0.01 to about 10 wt %, about to about 5 wt %, about 0.1 to about 30 wt %, about 0.1 to about 20 wt %, about 0.1 to about wt %, about 0.1 to about 5 wt %, about 1 to about 30 wt %, about 1 to about 20 wt %, about 1 to about 10 wt %, or about 1 to about 5 wt % of the exosome-enriched product comprising the intact bovine milk-derived exosomes, based on the weight of the powdered nutritional composition.

In view of the exosome-enriched product also containing whey protein, the exosome-enriched product may be the sole source of protein in the nutritional composition. Nevertheless, additional protein sources can be included in the nutritional composition. In a specific embodiment, the protein in the nutritional composition comprises whey protein concentrate, whey protein isolate, whey protein hydrolysate, acid casein, sodium caseinate, calcium caseinate, potassium caseinate, casein hydrolysate, milk protein concentrate, organic milk protein concentrate, milk protein isolate, milk protein hydrolysate, nonfat dry milk, condensed skim milk, soy protein concentrate, soy protein isolate, soy protein hydrolysate, pea protein concentrate, pea protein isolate, pea protein hydrolysate, collagen protein, collagen protein isolate, L-Carnitine, L-Lysine, taurine, lutein, rice protein concentrate, rice protein isolate, rice protein hydrolysate, fava bean protein concentrate, fava bean protein isolate, fava bean protein hydrolysate, collagen proteins, collagen protein isolates, meat proteins, potato proteins, chickpea proteins, canola proteins, mung proteins, *quinoa* proteins, amaranth proteins, chia proteins, hemp proteins, flax seed proteins, earthworm protein, insect protein, one or more amino acids and/or metabolites thereof, or combinations of two or more thereof.

The one or more amino acids, which may be described as free amino acids, can be any amino acid known for use in nutritional products. The amino acids may be naturally occurring or synthetic amino acids. In a specific embodiment, the one or more amino acids and/or metabolites thereof comprise one or more branched chain amino acids or metabolites thereof. Examples of branched chain amino acids include arginine, glutamine leucine, isoleucine, and valine.

In another specific embodiment, the one or more branched chain amino acids or metabolites thereof comprise leucic acid (HICA), keto isocaproate (KIC), 8-hydroxy-8-methylbutyrate (HMB), and combinations of two or more thereof.

The nutritional composition may comprise protein in an amount from about 1 wt % to about 30 wt % of the nutritional composition. More specifically, the protein may be present in an amount from about 1 wt % to about 25 wt % of the nutritional composition, including about 1 wt % to about 20 wt %, about 2 wt % to about 20 wt %, about 1 wt % to about 15 wt %, about 1 wt % to about 10 wt %, about 5 wt % to about 10 wt %, about 10 wt % to about 25 wt %, or about 10 wt % to about 20 wt % of the nutritional composition. Even more specifically, the protein comprises from about 1 wt % to about 5 wt % of the nutritional composition, or from about 20 wt % to about 30 wt % of the nutritional composition.

In another specific embodiment, the carbohydrate in the nutritional composition comprises fiber, human milk oligosaccharides (HMOs), maltodextrin, corn maltodextrin, organic corn maltodextrin, corn syrup, sucralose, cellulose gel, cellulose gum, gellan gum, inositol, carrageenan, fructooligosaccharides, maltodextrin, hydrolyzed starch, glucose polymers, corn syrup, corn syrup solids, rice-derived carbohydrates, sucrose, glucose, lactose, honey, sugar alcohols, isomaltulose, sucromalt, pullulan, potato starch, galactooligosaccharides, oat fiber, soy fiber, corn fiber, gum arabic, sodium carboxymethylcellulose, methylcellulose, guar gum, gellan gum, locust bean gum, konjac flour, hydroxypropyl methylcellulose, tragacanth gum, karaya gum, gum acacia, chitosan, arabinoglactins, glucomannan, xanthan gum, alginate, pectin, low methoxy pectin, high methoxy pectin, cereal beta-glucans, carrageenan, *psyllium*, inulin, fructooligosaccharides, or combinations of two or more thereof.

The nutritional composition may comprise carbohydrate in an amount from about 5 wt % to about 75 wt % of the nutritional composition. More specifically, the carbohydrate may be present in an amount from about 5 wt % to about 70 wt % of the nutritional composition, including about 5 wt % to about 65 wt %, about 5 wt % to about 50 wt %, about 5 wt % to about 40 wt %, about 5 wt % to about 30 wt %, about 5 wt % to about 25 wt %, about 10 wt % to about 65 wt %, about 20 wt % to about 65 wt %, about 30 wt % to about 65 wt %, about 40 wt % to about 65 wt %, about 40 wt % to about 70 wt %, or about 15 wt % to about 25 wt %, of the nutritional composition.

In another specific embodiment, the fat in the nutritional composition comprises coconut oil, fractionated coconut oil, soy oil, soy lecithin, corn oil, safflower oil, sunflower oil, palm olein, canola oil monoglycerides, lecithin, medium chain triglycerides, one or more fatty acids such as linoleic acid, alpha-linolenic acid, ARA, EPA, and/or DHA, fractionated coconut oil, soy oil, corn oil, olive oil, safflower oil, medium chain triglyceride oil (MCT oil), high gamma linolenic (GLA) safflower oil, palm oil, palm kernel oil, canola oil, marine oils, fish oils, algal oils, borage oil, cottonseed oil, fungal oils, omega-3 fatty acid, interesterified oils, transesterified oils, structured lipids, or combinations of two or more thereof. In a specific embodiment of the invention, the fat comprises a omega-3 fatty acid is selected from the group consisting of eicosapentaenoic acid, docosahexaenoic acid, arachidonic acid, and alpha-linolenic acid, and combinations of two or more thereof.

The nutritional composition may comprise fat in an amount of from about 0.5 wt % to about 30 wt % of the nutritional composition. More specifically, the fat may be present in an amount from about 0.5 wt % to about 10 wt %, about 1 wt % to about 30 wt % of the nutritional composition, including about 1 wt % to about 20 wt %, about 1 wt % to about 15 wt %, about 1 wt % to about 10 wt %, about 1 wt % to about 5 wt %, about 3 wt % to about 30 wt %, about 5 wt % to about 30 wt %, about 5 wt % to about 25 wt %, about 5 wt % to about 20 wt %, about 5 wt % to about 10 wt %, or about 10 wt % to about 20 wt % of the nutritional composition.

The concentration and relative amounts of the sources of protein, carbohydrate, and fat in the exemplary nutritional compositions can vary considerably depending upon, for example, the specific dietary needs of the intended user. In a specific embodiment, the nutritional composition comprises a source of protein in an amount of about 2 wt % to about 20 wt %, a source of carbohydrate in an amount of about 5 wt % to about 30 wt %, and a source of fat in an amount of about 0.5 wt % to about 10 wt %, based on the weight of the nutritional composition, and, more specifically, such composition is in liquid form. In another specific embodiment, the nutritional composition comprises a source of protein in an amount of about 10 wt % to about 25 wt %, a source of carbohydrate in an amount of about 40 wt % to about 70 wt %, and a source of fat in an amount of about 5 wt % to about 20 wt %, based on the weight of the nutritional composition, and, more specifically, such composition is in powder form.

In specific embodiments, the nutritional composition has a neutral pH, i.e., a pH of from about 6 to 8 or, more specifically, from about 6 to 7.5. In more specific embodiments, the nutritional composition has a pH of from about 6.5 to 7.2 or, more specifically, from about 6.8 to 7.1.

In a specific embodiment of the invention, the nutritional composition is administered in the form of a powder. In another specific embodiment, the nutritional composition is administered in the form of a liquid.

When the nutritional composition is a powder, for example, a serving size is from about g to about 60 g, such as 45 g, or 48.6 g, or 50 g, to be administered as a powder or to be reconstituted in from about 1 ml to about 500 ml of liquid, such as about 225 ml, or from about 230 ml to about 245 ml.

When the nutritional composition is in the form of a liquid, for example, reconstituted from a powder or manufactured as a ready-to-drink product, a serving ranges from about 1 ml to about 500 ml, including from about 110 ml to about 500 ml, from about 110 ml to about 417 ml, from about 120 ml to about 500 ml, from about 120 ml to about 417 ml, from about 177 ml to about 417 ml, from about 207 ml to about 296 ml, from about 230 m to about 245 ml, from about 110 ml to about 237 ml, from about 120 ml to about 245 ml, from about 110 ml to about 150 ml, and from about 120 ml to about 150 ml. In specific embodiments, the serving is about 1 ml, or about 100 ml, or about 225 ml, or about 237 ml, or about 500 ml.

In a specific embodiment, the nutritional composition comprises protein, carbohydrate, fat, and one or more nutrients selected from the group consisting of vitamins, minerals, and trace minerals.

Non-limiting examples of vitamins include vitamin A, vitamin B12, vitamin C, vitamin D, vitamin E, vitamin K, thiamine, riboflavin, pyridoxine, niacin, folic acid, pantothenic acid, biotin, choline, inositol, and/or salts and derivatives thereof, and combinations thereof. Non-limiting examples of minerals and trace minerals include calcium, phosphorus, magnesium, zinc, manganese, sodium, potassium, molybdenum, chromium, iron, copper, and/or chloride, and combinations thereof.

The nutritional composition may also comprise one or more components to modify the physical, chemical, aesthetic, or processing characteristics of the nutritional composition or serve as additional nutritional components. Non-limiting examples of additional components include preservatives, emulsifying agents (e.g., lecithin), buffers, sweeteners including artificial sweeteners (e.g., saccharine, aspartame, acesulfame K, sucralose), colorants, flavorants, thickening agents, stabilizers, and so forth.

The following Examples demonstrate various embodiments of the invention.

EXAMPLES

Example 1: Preparation and Characterization of Exosome-enriched Products

This example describes a method of preparing an exosome-enriched product from cheese whey. The cheese whey was provided by adding rennet enzyme to bovine milk, resulting in enzymatic coagulation of casein and production of sweet cheese whey, as described above.

An exosome-enriched product containing about $10^8$ to $10^{14}$ intact bovine milk-derived exosomes per gram of the exosome-enriched product was prepared by cascade membrane filtration. First, 1,000 L of sweet cheese whey was processed using tandem multiple ceramic filtration steps. The first microfiltration MF step employed a membrane with a molecular weight cut off of 1.4 μm, which yielded a first retentate R1 and a first permeate P1. The first permeate P1 was then subjected to a ultrafiltration step UF with a molecular weight cut off of 0.14 μm, which yielded a second retentate R2 and second permeate P2. About 5 volumes of water was added to one volume of the second retentate R2, and the diluted retentate was then passed through the 0.14 μm UF membrane again to remove at least part of the lactose and minerals. The resulting retentate R3 was then combined with an equal volume of water and diafiltered using a 10 kDa membrane to produce a fourth retentate R4. The retentate R4 was diluted with a volume of water five times that of the fourth retentate R4 and diafiltered a second time using the 10 kDa membrane to yield a concentrated retentate, R5. The lactose-free exosome-enriched product R5 was pasteurized at 70° C. for 15 seconds to ensure microbiological stability in order to yield a pasteurized exosome-enriched product R6. A portion of the pasteurized exosome-enriched product R6 was subjected to evaporation at about 65° C. to increase the solids content up to 17-18% and then spray-dried at 185° C./85° C. to obtain a exosome-enriched spray-dried product, SP. Another portion of the pasteurized exosome-enriched product R6 was freeze dried at −50° C. and 0.5 mbar to obtain a exosome-enriched freeze-dried product, FP.

The starting cheese whey, the second retentate R2, and the exosome-enriched products comprising intact bovine milk derived exosomes prepared as described above were analyzed to determine lactose and protein content, as set forth in Table 1 below.

TABLE 1

Lactose and protein composition of the exosome-enriched product.

| Fractions | Protein % (by Milkoscan) | Protein % (by LECO) | Lactose % | Total Solids % |
|---|---|---|---|---|
| W | 1.39 ± 0.02 | 0.93 | 4.48 ± 0.01 | 6.33 ± 0.03 |
| R2 | 1.82 ± 0.01 | 1.13 | 3.41 ± 0.02 | 5.62 ± 0.01 |
| R6 | 5.63 ± 0.04 | 6.87 | 0 | 7.10 ± 0.03 |
| SP | — | 80.34 | 0 | Powder |
| FP | — | 78.45 | 0 | Powder |

Composition analysis of different fractions and exosome-enriched powders: W = cheese whey. R2 = final exosome-enriched liquid fraction. R6 = final exosome-enriched liquid fraction. SP = spray-dried powder. FP = freeze-dried powder.

The amount of fat, protein, lactose, and total solids of the collected samples from each of the fractions referred to in Table 1 were determined by Fourier transform infrared (FTIR) spectroscopy using a Bentley Instruments Dairy Spec FT (Bentley Instruments, Inc., Chaska, MN, USA). The Bentley Instruments Dairy Spec FT captures the complete infrared absorption spectrum of the milk sample for component analysis. This particular technology exceeds the IDF 141C:2000 Standard and ICAR requirements for Milk Component Measurement and uses AOAC approved methodology, thus providing a non-destructive, reliable and precise measurement.

The results presented in Table 1 surprisingly demonstrate that the pasteurized exosome-enriched product R6, the spray-dried exosome-enriched product SP, and the freeze-dried exosome-enriched product FP were all lactose-free. Further, the protein content in the pasteurized exosome-enriched product R6 increased almost 7 times with respect to the cheese whey starting material, and about 6 times with respect to the exosome-enriched second retentate R2. In addition, about 80% of the dry matter of the powders was protein and about 15% of the dry matter was fat, which is consistent with the lipid-protein nature of exosomes.

In order to gain further insight on the exosome content of the pasteurized exosome-enriched product R6 and the exosome-enriched SP and FP powders, a Western blot analysis was performed to detect the presence of the exosome-specific marker TSG101. The exosome-enriched product R6 and the exosome-enriched SP and FP powders showed the TSG101 band of interest at around 50 kDa. Notably, the TSG101 biomarker was not detectable in cheese whey, despite equal amounts of protein being loaded per lane. This indicates that the pasteurized exosome-enriched product R6 and the exosome-enriched SP and FP powders produced according to the process described above are significantly enriched in milk exosomes.

Transmission electron microscopy (TEM) was also used for purposes of assessing the presence of exosomes in the pasteurized exosome-enriched product R6, and in the exosome-enriched SP and FP powders. TEM is a technique which can be used for the direct visualization of nanosized structures, such as exosomes. The application of uranyl acetate as a negative dye was used to study the impact of thermal treatments, such as pasteurization, evaporation, spray-drying, and freeze-drying, on the exosome structure of the exosomes in the pasteurized lactose-free exosome-enriched product R6, and in the final lactose-free exosome-enriched SP and FP products. Briefly, the uranyl acetate acts as a negative dye, which stains the background and leaves the intact vesicular structures, such as intact exosomes, unstained and highly visible.

The lactose-free exosome-enriched SP and FP powders prepared as described above were resuspended in water and 3 microliters of each sample were placed on a Formvar® coated grid and stained with 2% uranyl acetate for 5 minutes. The exosome-enriched R5 and R6 products, prepared as described above, were placed undiluted on a Formvar® coated grid and stained with 2% uranyl acetate for 5 minutes. The samples were visualized at a magnification of ×25,000. TEM images of the R5 and R6 exosome-enriched products, and the exosome-enriched SP and FP powders showed that the intact exosomes were present at high concentration. Remarkably, none of the thermal treatments that were applied led to significant exosome damage. These results demonstrate that the process described above can isolate and stabilize a significant amount intact milk exosomes from cheese whey.

The exosome-enriched products comprising intact bovine milk-derived exosomes prepared as described above were also analyzed to determine nucleic acid content. More specifically, the exosome-enriched SP and FP powders and the pasteurized exosome-enriched product R6 were analyzed in order to determine their total RNA content (μg), total miRNA content (μg), and miRNA as a percentage of the total RNA, as set forth in Table 2 below. 10 mg of each sample were extracted and analyzed using a Bioanalyzer 2100/Eukaryote Total RNA Nano Chip. The exosome-enriched SP and FP powders and the pasteurized exosome-enriched product R6 displayed high amounts of both RNA and miRNA, however the exosome-enriched SP powder showed higher miRNA content than the exosome-enriched FP powder. This indicates that spray-drying may be a better stabilization strategy for providing an exosome-enriched product in powder form.

TABLE 2

Nucleic acid composition of the exosome-enriched product.

| | Total RNA content (μg) | miRNA % (of total nucleic acids) | miRNA content (μg) |
|---|---|---|---|
| R6 | 5.50 | 67.1 | 3.68 |
| SP | 5.09 | 72.5 | 3.69 |
| FP | 2.51 | 76.1 | 1.91 |

The exosome-enriched products comprising intact bovine milk-derived exosomes were also analyzed to determine lipid composition. Ultra-performance liquid chromatography coupled to time-of-flight mass spectrometry analysis (UPLC-TOF-MS) was performed to analyze the lipid content of the lactose-free exosome-enriched products described above. The results are set forth in Table 3 below and are expressed as a percentage of total lipids.

TABLE 3

Lipid composition of the lactose-free exosome-enriched product.

| LIPID SPECIE | R6 % of total lipids | R6 mg/g powder | SP % of total lipids | SP mg/g powder | FP % of total lipids | FP mg/g powder |
|---|---|---|---|---|---|---|
| Triacylglicerols | 76.9 | NA (liquid) | 70.6 | 117.4 | 70.7 | 75.1 |
| Phosphatidylcholine | 6.4 | NA (liquid) | 7.5 | 12.5 | 7.9 | 8.3 |
| Phosphatidylethanolamine | 5.0 | NA (liquid) | 6.7 | 11.1 | 6.0 | 6.3 |
| Sphingomyelin | 3.8 | NA (liquid) | 4.9 | 8.2 | 6.6 | 7.0 |
| Gangliosides (GD3) | 1.9 | NA (liquid) | 2.7 | 4.4 | 2.4 | 2.5 |
| Phosphatidylserine | 1.8 | NA (liquid) | 2.0 | 3.4 | 2.0 | 2.1 |
| Cholesterol esters | 1.2 | NA (liquid) | 1.4 | 2.4 | 1.1 | 1.2 |
| Ceramide dihexoside | 0.9 | NA (liquid) | 1.3 | 2.2 | 1.0 | 1.1 |
| Dihydrosphingomyelin | 0.6 | NA (liquid) | 0.8 | 1.3 | 0.8 | 0.8 |
| Cholesterol (free) | 0.4 | NA (liquid) | 0.5 | 0.8 | 0.4 | 0.4 |
| Ceramide monohexoside | 0.3 | NA (liquid) | 0.4 | 0.7 | 0.4 | 0.4 |
| Ether-linked phosphatidylethanolamine | 0.2 | NA (liquid) | 0.2 | 0.4 | 0.2 | 0.2 |
| Ceramide | 0.1 | NA (liquid) | 0.2 | 0.3 | 0.2 | 0.2 |
| Gangliosides (GM3) | 0.1 | NA (liquid) | 0.2 | 0.3 | 0.1 | 0.1 |
| Phosphatidylinositol | 0.1 | NA (liquid) | 0.2 | 0.3 | 0.1 | 0.1 |
| Lysophosphatidylethanolamine | 0.1 | NA (liquid) | 0.1 | 0.2 | 0.1 | 0.1 |
| Lysophosphatidylcholine | 0.1 | NA (liquid) | 0.1 | 0.2 | 0.1 | 0.1 |
| Dihydroceramide | 0.1 | NA (liquid) | 0.1 | 0.1 | 0.1 | 0.1 |
| Free fatty acids | Traces | Traces | Traces | Traces | Traces | Traces |
| Total lipid content (1%, on a dry basis) | NA | | NA | | NA | |

The protein compositions of the exosome-enriched products were also determined. Specifically, the protein composition was determined by LC-MS/MS and mass spectra were searched in Proteome Discoverer v1.4 (database Bos Taurus, Uniprot 06/19+Proteomics contaminants database). The results of several proteins of interest are set forth in Table 4 and surprisingly demonstrate that caseins were present at very low levels (e.g., only 0.04% of a α-S2-casein was detected). In addition, the results demonstrate that significant amounts of bioactive proteins (i.e., lactoferrin and immunoglobulins) were detected. The results are expressed as % of total proteins identified.

TABLE 4

Protein composition of the lactose-free exosome-enriched product.

| PROTEIN | R6 % of total proteins | R6 mg/g powder | SP % of total proteins | SP mg/g powder | FP % of total proteins | FP mg/g powder |
|---|---|---|---|---|---|---|
| β-lactoglobulin | 56.40 | NA (liquid) | 58.97 | 471.76 | 59.24 | 473.92 |
| Serum albumin | 12.12 | NA (liquid) | 11.77 | 94.16 | 12.32 | 98.56 |
| Antibodies (IgG, IgM, IgA) | 6.33 | NA (liquid) | 6.63 | 53.04 | 6.42 | 51.36 |
| α-lactalbumin | 5.00 | NA (liquid) | 4.55 | 36.4 | 4.59 | 36.72 |
| Lactoferrin | 3.53 | NA (liquid) | 3.12 | 24.96 | 3.18 | 25.44 |
| Butyrophilin | 2.18 | NA (liquid) | 1.90 | 15.2 | 1.06 | 8.48 |
| Lactadherin | 1.67 | NA (liquid) | 1.45 | 11.6 | 1.52 | 12.16 |
| Xanthine dehydro-genase/oxidase | 1.45 | NA (liquid) | 1.36 | 10.88 | 1.40 | 11.2 |
| Transferrin | 1.27 | NA (liquid) | 1.05 | 8.4 | 0.98 | 7.84 |
| Lactoperoxidase | 0.54 | NA (liquid) | 0.53 | 4.24 | 0.59 | 4.72 |
| Vitamin D-binding protein | 0.17 | NA (liquid) | 0.15 | 1.2 | 0.15 | 1.2 |
| Osteopontin | 0.18 | NA (liquid) | 0.15 | 1.2 | 0.15 | 1.2 |
| α-S1-casein | 0.29 | NA (liquid) | 0.13 | 1.04 | 0.21 | 1.68 |
| κ-casein | 0.06 | NA (liquid) | 0.04 | 0.32 | 0.05 | 0.4 |
| β-casein | 0.04 | NA (liquid) | 0.03 | 0.24 | 0.03 | 0.24 |
| α-S2-casein | 0.02 | NA (liquid) | 0.01 | 0.08 | 0.01 | 0.08 |
| Total casein | 0.41 | NA (liquid) | 0.21 | 1.68 | 0.30 | 2.4 |
| Total protein content (1%, on a dry basis) | NA | | NA | | NA | |

Example 2: Enhanced Chondrocyte Proliferation

This example demonstrates that an exosome-enriched product containing intact bovine milk-derived exosomes enhances human chondrocyte proliferation, which is required in order to promote linear bone growth. This was shown by evaluating chondrocyte viability and proliferation through MTT assay (a colorimetric assay for assessing cell metabolic activity employing the tetrazolium dye MTT, 3-(4,5-dimethylthiazol-2-yl)-2,5-diphenyltetrazolium bromide) using C28/12 human chondrocyte cells.

The 028/12 human chondrocyte cells were grown at 37° C. in Dulbecco's Modified Eagle's Medium (DMEM) supplemented with 10% fetal bovine serum and antibiotics (50 U/ml penicillin and 50 μg/ml streptomycin) in 5% CO2 and 95% air. The cells were subcultured after reaching 70-90% confluence.

The C28/12 human chondrocyte cells were incubated with 5 μg/mL, 15 μg/mL, or 30 μg/mL of the exosome-enriched product for 24-48 hours.

After the treatment of the cells with the exosome-enriched product, 50 μg/mL MTT was added to the cells at 37° C. for 30 minutes. Following incubation, the MTT-containing medium was discarded and acidic isopropanol (40 mM HCl in isopropanol) was added to dissolve the formazan crystals. The optical densities (OD) were measured at 570 nm using an absorbance microplate reader. The viability of the cells was normalized, according to the OD value in untreated group.

As evidenced by the results in FIG. 1, when compared to the control, i.e. 0 μg/mL of the exosome-enriched product, chondrocytes incubated with the exosome-enriched product showed a statistically significant increase in proliferation capacity at both 24 and 48 hours. These results indicate that the exosome-enriched product containing intact bovine milk-derived exosomes was able to increase chondrocyte proliferation, a key element of linear bone growth.

Example 3: Cell Cycle Analysis

This example further demonstrates that the enriched-exosome product containing intact bovine milk-derived exosomes enhances chondrocyte proliferation, and thus confirms the results of Example 2. This was shown by cell cycle distribution analysis through propidium iodide staining and flow cytometry using C28/12 human chondrocyte cells.

This method relied on the fact that DNA of any cell can be stained by propidium iodide. Propidium iodide binds in proportion to the amount of DNA present in the cell. In mammals, the cell cycle consists of four successive phases: the S phase, the M phase, and the G1 and G2 phases. In the S phase, the cell replicates its DNA, while in mitosis (M phase), the cell divides its replicated DNA into two daughter cells. The two gap phases, G1 and G2, separate DNA replication from mitosis; G1 extends from mitosis to the next round of DNA replication, while G2 is the gap between the S phase and the next M phase. The G1 phase is particularly important, given that it will determine whether or not a cell commits to division. A cell will only move from the G1 phase to the S phase when it is signaled to proliferate.

Since a cell's decision to proliferate is made in the G1 phase immediately before initiating DNA synthesis and progressing through the rest of the cell cycle, the detection of DNA in each single cell allows for the determination of the status of cell proliferation/growth regulation in cell culture experiments. Thus, cells that are in S phase will have more DNA than cells in G1. They will take up proportionally more dye and will fluoresce more brightly until they have doubled their DNA content. The cells in G2 will be approximately twice as bright as cells in G1.

The 028/12 human chondrocyte cells were grown at 37° C. in Dulbecco's Modified Eagle's Medium (DMEM) supplemented with 10% fetal bovine serum and antibiotics (50 U/ml penicillin and 50 μg/ml streptomycin) in 5% CO2 and 95% air, and were subcultured after reaching 70-90% confluence. The 028/12 human chondrocyte cells were incubated with 5 μg/mL, 15 μg/mL, or 30 μg/mL of the exosome-enriched product for 24-48 hours.

Figure 2:
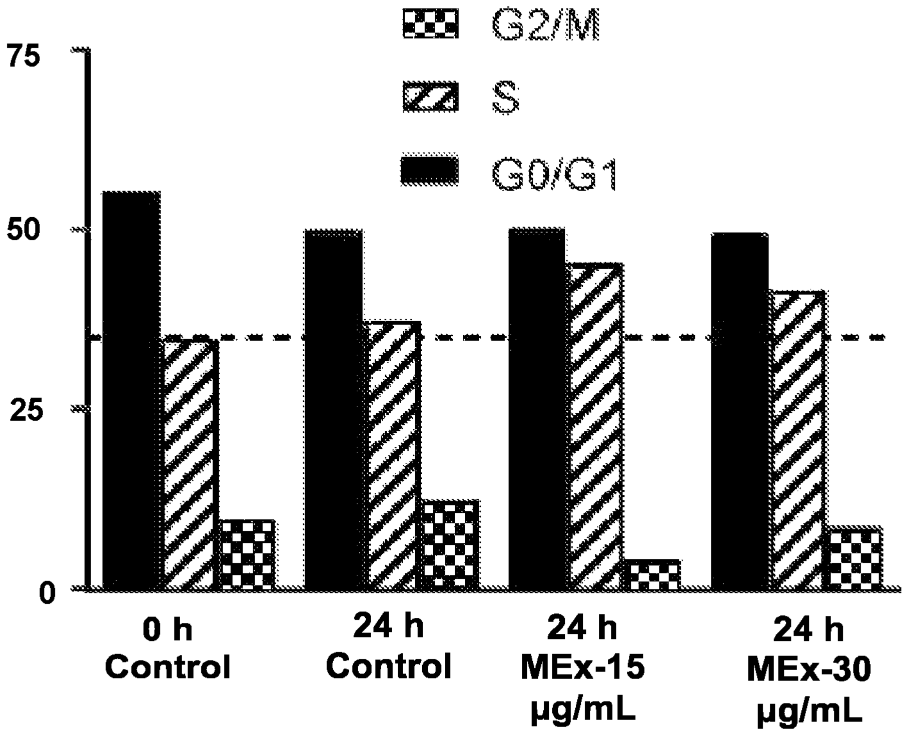
FIG. 2 illustrates a cell cycle distribution analysis of 028/12 human chondrocyte cells incubated with increasing amounts of an exosome-enriched product containing intact bovine milk-derived exosomes, as described in Example 3.

FIG. 2 sets forth the percentage of cells transitioning from the G0/G1 phase to the S phase, and from the S phase to the G2/M phase, when incubated with either 15 μg/mL of the milk exosomes or 30 μg/mL of the milk exosomes over a period of 24 hours. These results are compared with a control which did not have any exosome treatment and were similarly incubated. As shown in FIG. 2, the chondrocyte cell cultures incubated with milk exosomes showed a significant increase in the percentage of cells entering phase S after 24 hours of incubation as compared with the control at both 0 hours and after 24 hours of incubation. More specifically, about 45.40% of the cells incubated with 15 μg/mL of the milk exosomes for 24 hours transitioned from the G0/G1 phase to the S phase, as compared to about 37.42% of cells in the control at 24 hours. With regard to the cells incubated with 30 μg/mL of the milk exosomes, about 41.64% transitioned from the G0/G1 phase to the S phase. As discussed above, the transition from G1 phase to S phase is required for cell division. These results thus indicate and confirm that the exosome-enriched product containing intact bovine milk-derived exosomes enhance proliferative activity of chondrocytes. The consumption of the exosome-enriched product containing intact bovine milk-derived exosomes can thus be used to increase height and promote linear bone growth in a pediatric subject.

Example 4: Animal Model

This example evaluates the effect of the chronic administration of a diet including an exosome-enriched product comprising intact bovine milk-derived exosomes on the regulation of growth plate activity during a catch-up growth period using an animal model of growth retardation or nutritional dwarfing.

The nutritional dwarfing model is based on developing a nutritional stress in weanling male rats placed on restricted intake (30% of normal intake) of a control diet for three weeks. This restriction period was followed by another two weeks of catch-up growth with full access to the experimental diets.

During the restriction period, the animals were divided into two groups. Non-restricted rats (NR group) were fed with a standard rodent diet ad libitum during the entire study period, and more specifically AlN93G for the first 3 weeks and AlN93M for the following 2 weeks. The AlN93G diet is a rodent diet specifically designed to provide nutrients in adequate concentrations for young (up to 4 weeks old) rat or mouse populations, and the AlN93M diet is a rodent diet specifically designed to provide nutrients in adequate concentrations for rodents older than 4 weeks of age.

Restricted rats (RR group) received 70% of the amount of food consumed by the NR group for 3 weeks. On day 21, the restricted group was further divided into four subgroups. A restricted RR subgroup, RRR, continued receiving 70% of the amount of food consumed by the NR group for an additional 2 weeks. The other 3 RR subgroups (RRC, RRE1, and RRE2) were re-fed ad libitum, with different experimental diets for two weeks, i.e., the re-feeding period, following restriction. The RRC, RRE1 and RRE2 diets were designed to provide similar energetic and protein content. However, the RRE1 and REE2 diets were supplemented with an exosome-enriched product containing intact bovine milk-derived exosomes. The RRE1 group consumed a diet supplemented with 0.45 g exosome-enriched product/kg and the RRE2 group consumed a diet supplemented with 4.5 g exosome-enriched product/kg. The compositions of the experimental diets used in this study are provided in Table 5 below.

TABLE 5

Compositions of experimental diets.

| | AIN93G | AIN93M | RRC | RRE1 | RRE2 |
|---|---|---|---|---|---|
| Carbohydrate (g/100 g diet) | 67.4 | 78.5 | 59.5 | 59.5 | 59.5 |
| Protein (g/100 g diet) | 17.9 | 14.0 | 18.6 | 18.6 | 18.6 |
| Fat (g/100 g diet) | 7.0 | 4.0 | 11.6 | 11.6 | 11.6 |
| Exosomes (mg/100 g diet) | — | — | — | 45 | 450 |

After sacrificing the animals, tibias were carefully removed from each animal. Growth plate morphology in the isolated appendicular (tibia) bones was analyzed utilizing a micro-CT technical approach to determine key growth plate markers related to growth plate activity, namely thickness, surface and volume. Each sample was measured with a commercially available cabinet cone-beam microCT (μCT 100, SCANCO Medical AG, Bruttisellen, Switzerland), which operates with a cone beam originating from a 5 μm focal-spot X-ray tube. The photons are detected by a CCD-based area detector and the projection data are computer-reconstructed into an e.g. 2048×2048 image matrix.

Remarkably, in the present study, the level of food restriction imposed was severe enough to decrease the normal bone development in restricted animals.

Figure 3:
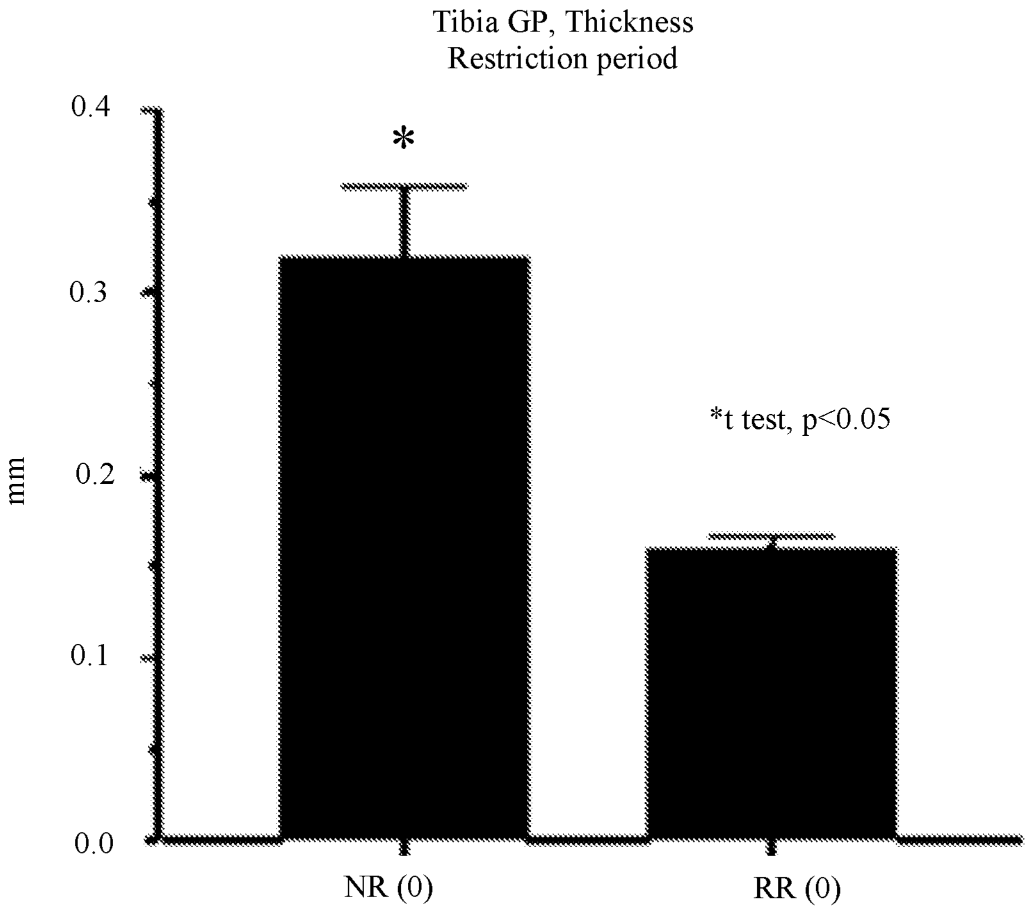
FIG. 3 illustrates the effect of growth inhibiting conditions on growth plate thickness in stunted Sprague-Dawley rats that received 70% of the amount of food consumed by well-nourished rats, as described in Example 4.
Figure 4:
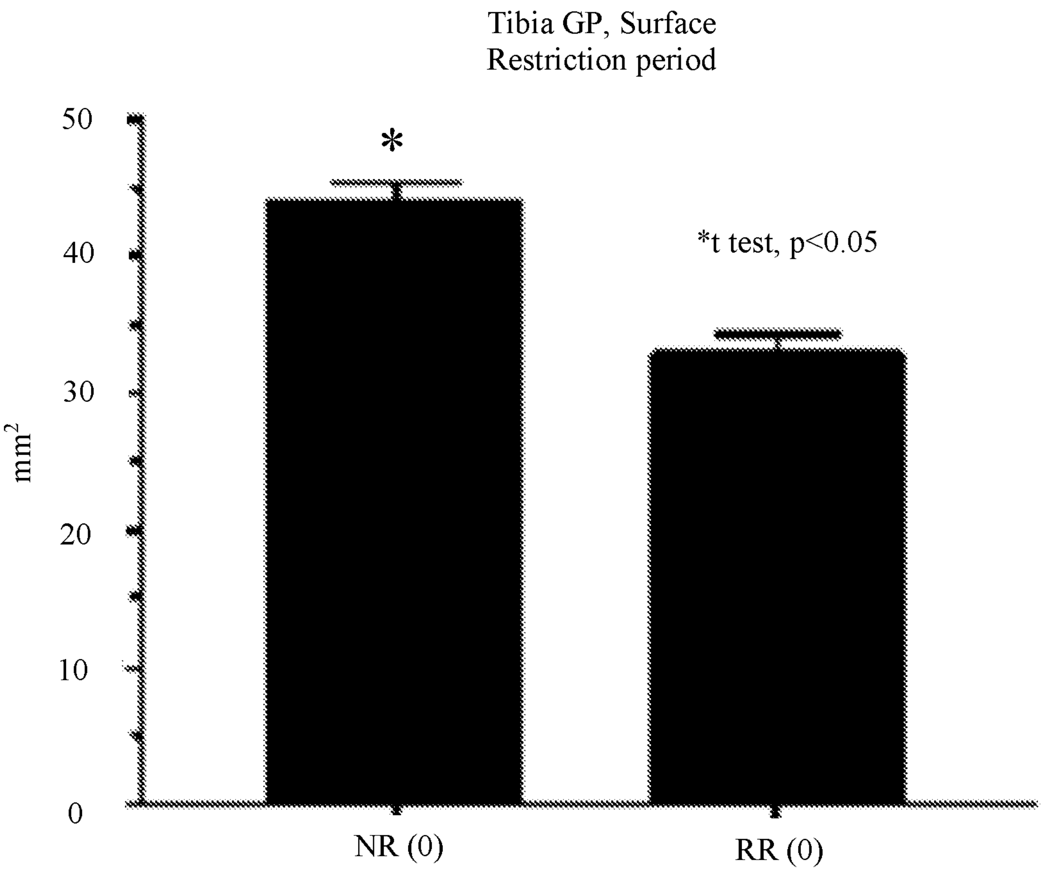
FIG. 4 illustrates the effect of growth inhibiting conditions on growth plate surface in stunted Sprague-Dawley rats that received 70% of the amount of food consumed by well-nourished rats, as described in Example 4.
Figure 5:
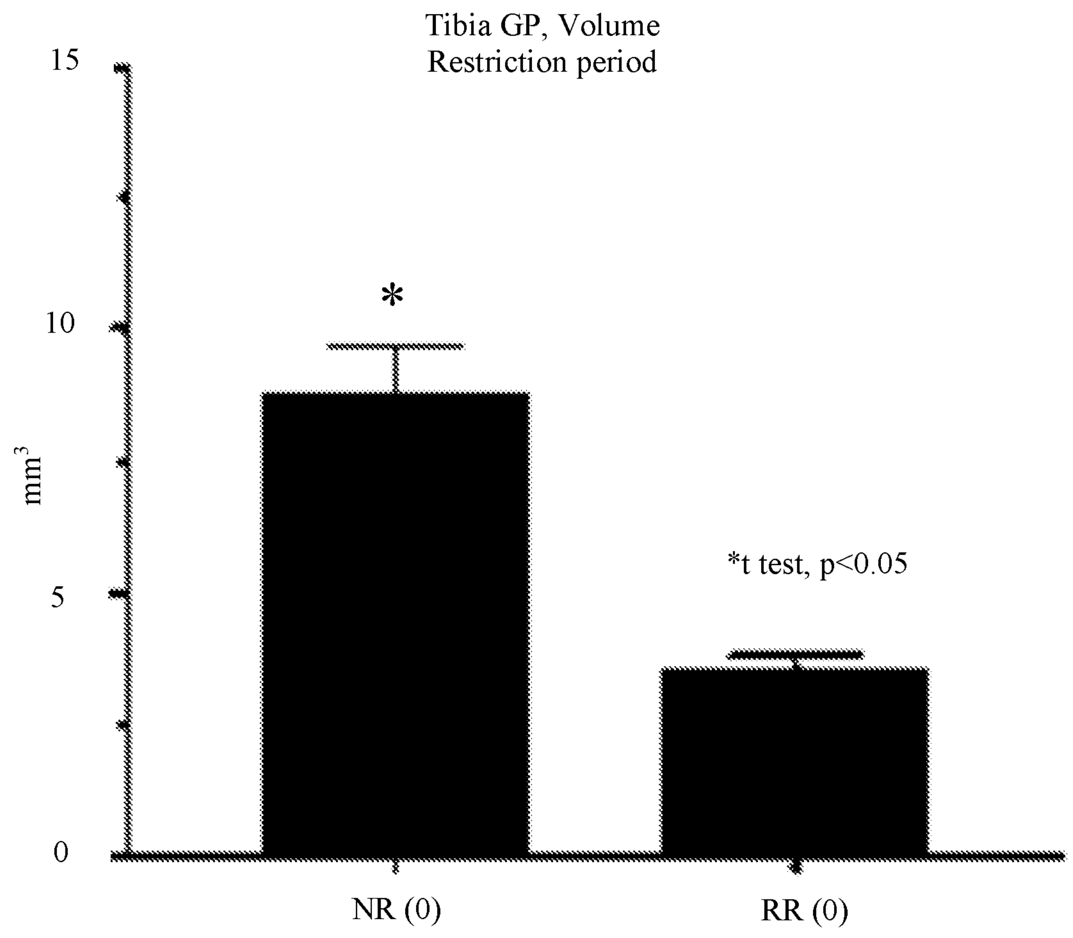
FIG. 5 illustrates the effect of growth inhibiting conditions on growth plate volume in stunted Sprague-Dawley rats that received 70% of the amount of food consumed by well-nourished rats, as described in Example 4.
Figure 6:
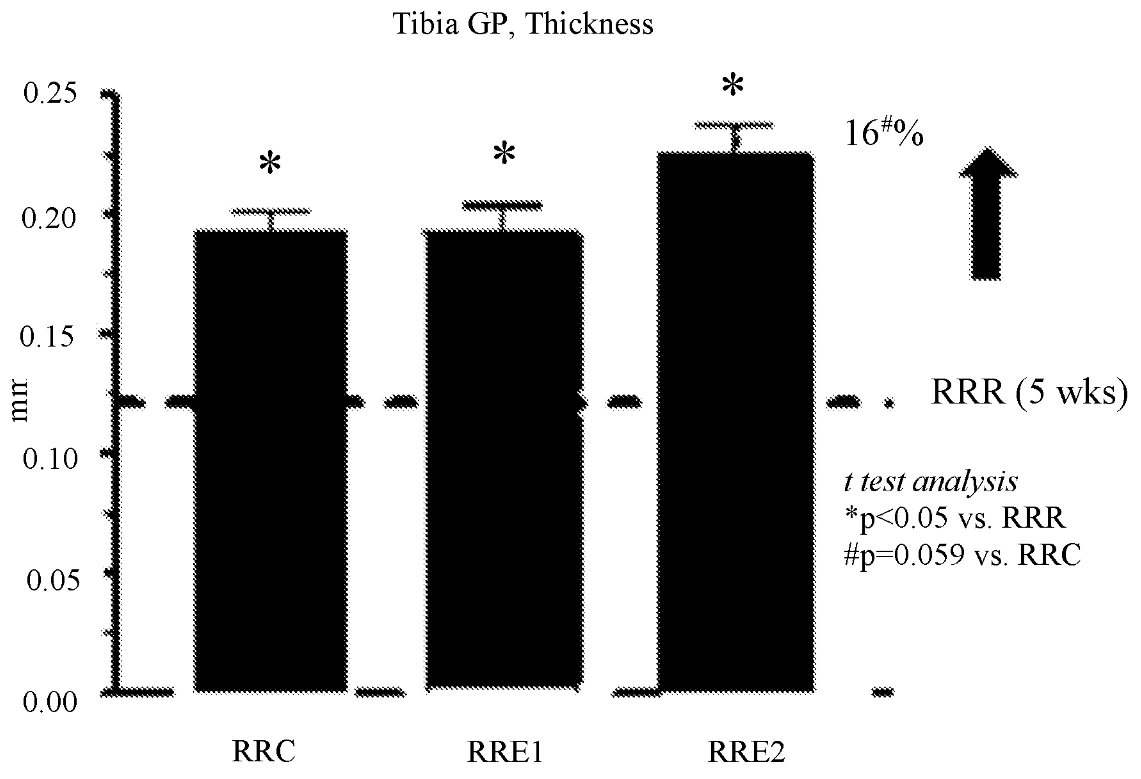
FIG. 6 illustrates the effect of catch-up growth on growth plate thickness in stunted rats that consumed a diet with an exosome-enriched product comprising intact bovine milk-derived exosomes, as described in the Example 4.
Figure 7:
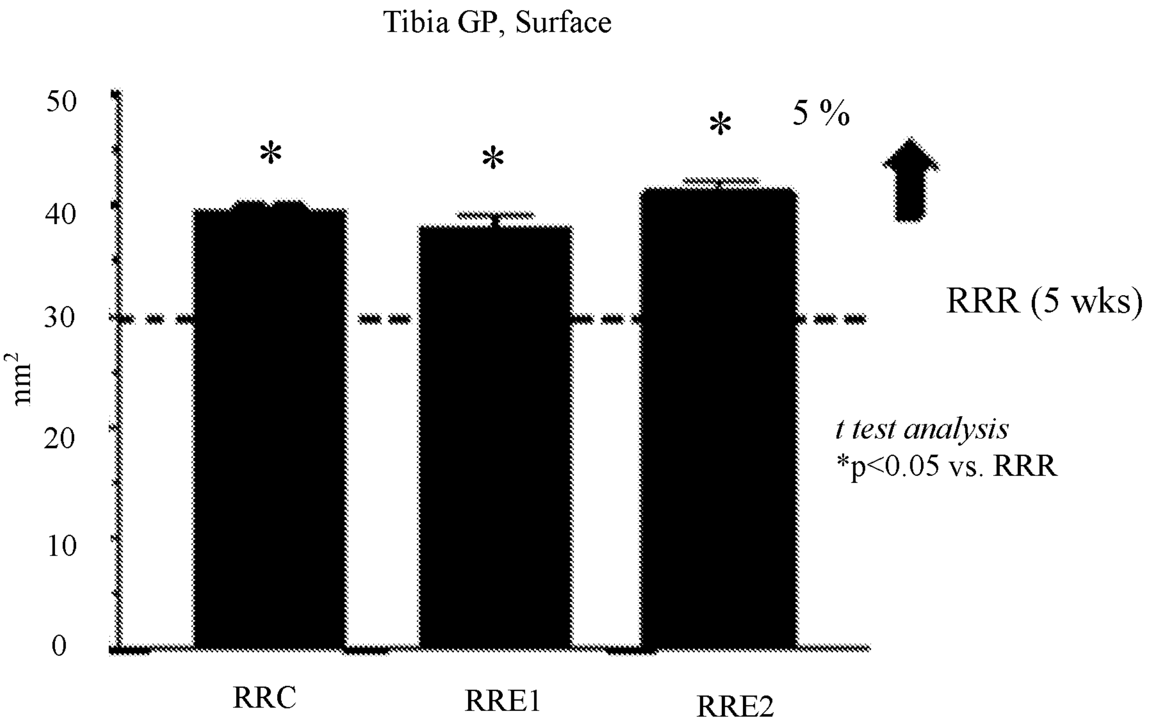
FIG. 7 illustrates the effect of catch-up growth on growth plate surface in stunted rats that consumed a diet with an exosome-enriched product comprising intact bovine milk-derived exosomes, as described in the Example 4.
Figure 8:
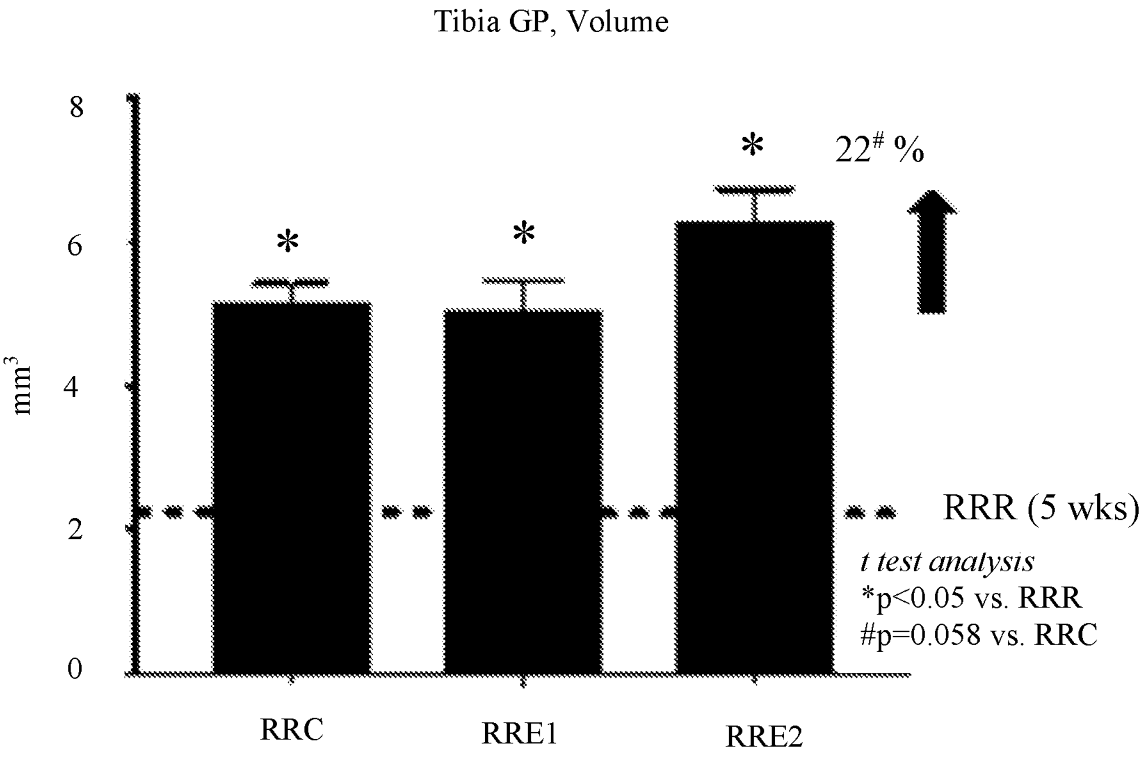
FIG. 8 illustrates the effect of catch-up growth on growth plate volume in stunted rats that consumed a diet with an exosome-enriched product comprising intact bovine milk-derived exosomes, as described in the Example 4.

After the three-week food restriction period, growth plate activity related markers, i.e., thickness, surface and volume, were significantly lower in restricted rats as compared to non-restricted rats (FIGS. 3-5). These results indicate that in the critical period for achieving an adequate longitudinal bone growth, nutritional stunting process resulted in growth deceleration by delaying growth plate senescence. The negative effects on bone status promoted by the food restriction period were partially recovered during the re-feeding period. However, the recovery degree was significantly different depending on the diet used during the catch-up growth (FIGS. 6-8).

Animals fed an RRE2 diet showed a significantly higher growth plate thickness (approximately 16%) and volume (approximately 22%) than the animals fed on the RRC diet. Successful nutritional-induced catch up growth by the administration of an exosome-enriched product comprising intact bovine milk-derived exosomes are effective to correct the growth deficiency over time and to recover the linear growth potential in stunted subjects.

These results demonstrate that the intake of an exosome-enriched product comprising intact bovine milk-derived exosomes improves growth plate activity during the catch-up period. Thus, administration of an exosome-enriched product comprising intact bovine milk-derived exosomes to children with stunted growth for age by nutritional restriction can provide improved longitudinal bone growth and height during the period of bone accrual, and may also confer bone strength advantages, not only in youth, but also throughout the duration of life.

In summary, the exosome-enriched product containing intact bovine milk-derived exosomes enhances chondrocyte viability and proliferative activity. Administration of such an exosome-enriched product is thus useful for preventing, reducing and/or treating linear bone growth restriction in pediatric subjects, caused by inadequate nutrition and/or treatments with glucocorticoids or chemotherapeutic agents. Additionally, the MF, UF, and DF steps provide an efficient method of obtaining the exosome-enriched product containing intact bovine milk-derived exosomes from cheese whey. Such a method will be useful for large-scale production of exosome-enriched products.

The specific embodiments and examples described herein are exemplary only and are not limiting to the invention defined by the claims.

What is claimed is:

1. A method of increasing height and/or promoting linear bone growth in a pediatric subject comprising enterally administering an exosome-enriched product comprising intact bovine milk-derived exosomes to the pediatric subject in need thereof.

2. The method of claim 1, wherein the exosome-enriched product comprising the intact bovine milk-derived exosomes is administered to the pediatric subject at a dose of about 0.01 to about 30 g.

3. The method of claim 1, wherein the pediatric subject is a child at the age of about 1 year old to about 15 years old.

4. The method of claim 1, wherein the pediatric subject is suffering from linear bone growth restriction.

5. The method of claim 1, wherein the exosome-enriched product comprises at least 0.001 wt % exosomes.

6. The method of claim 5, wherein at least about 50 wt % of the exosomes in the exosome-enriched product are intact.

7. The method of claim 5, wherein at least about 75 wt % of the exosomes in the exosome-enriched product are intact.

8. The method of claim 5, wherein at least about 90 wt % of the exosomes in the exosome-enriched product are intact.

9. The method of claim 1, wherein the exosome-enriched product is lactose-free.

10. The method of claim 1, wherein the exosome-enriched product comprising intact bovine milk-derived exosomes is administered to the pediatric subject in a nutritional composition comprising protein, carbohydrate, and/or fat.

11. The method of claim 10, wherein the nutritional composition comprises from about 0.001 to about 30 wt % of the exosome-enriched product comprising the intact bovine milk-derived exosomes, based on the weight of the nutritional composition.

12. The method of claim 10, wherein the protein comprises whey protein concentrate, whey protein isolate, whey protein hydrolysate, acid casein, sodium caseinate, calcium caseinate, potassium caseinate, casein hydrolysate, milk protein concentrate, organic milk protein concentrate, milk protein isolate, milk protein hydrolysate, nonfat dry milk, condensed skim milk, soy protein concentrate, soy protein isolate, soy protein hydrolysate, pea protein concentrate, pea protein isolate, pea protein hydrolysate, collagen protein, collagen protein isolate, rice protein concentrate, rice protein isolate, rice protein hydrolysate, fava bean protein concentrate, fava bean protein isolate, fava bean protein hydrolysate, collagen proteins, collagen protein isolates, meat proteins, potato proteins, chickpea proteins, canola proteins, mung proteins, *quinoa* proteins, amaranth proteins, chia proteins, hemp proteins, flax seed proteins, earthworm protein, insect protein, or combinations of two or more thereof.

13. The method of claim 10, wherein the nutritional composition further comprises one or more branched chain amino acids or metabolites thereof.

14. The method of claim 13, wherein the one or more branched chain amino acids or metabolites thereof comprises leucic acid (HICA), keto isocaproate (KIC), β-hydroxy-β-methylbutyrate (HMB), or a combinations of two or more thereof.

15. The method of claim 10, wherein the carbohydrate comprises fiber, human milk oligosaccharides (HMOs), maltodextrin, corn maltodextrin, organic corn maltodextrin, corn syrup, sucralose, cellulose gel, cellulose gum, gellan gum, inositol, carrageenan, fructooligosaccharides, hydrolyzed starch, glucose polymers, corn syrup, corn syrup solids, rice-derived carbohydrates, sucrose, glucose, lactose, honey, sugar alcohols, isomaltulose, sucromalt, pullulan, potato starch, galactooligosaccharides, oat fiber, soy fiber, corn fiber, gum arabic, sodium carboxymethylcellulose, methylcellulose, guar gum, locust bean gum, konjac flour, hydroxypropyl methylcellulose, tragacanth gum, karaya gum, gum acacia, chitosan, arabinoglactins, glucomannan, xanthan gum, alginate, pectin, low methoxy pectin, high methoxy pectin, cereal beta-glucans, psyllium, inulin, or combinations of two or more thereof.

16. The method of claim 10, wherein the fat comprises coconut oil, fractionated coconut oil, soy oil, soy lecithin, corn oil, safflower oil, sunflower oil, palm olein, canola oil monoglycerides, lecithin, medium chain triglycerides, one or more fatty acids such as linoleic acid, alpha-linolenic acid, arachidonic acid, eicosapentaenoic acid, and/or docosahexaenoic acid, olive oil, medium chain triglyceride oil (MCT oil), high gamma linolenic (GLA) safflower oil, palm oil, palm kernel oil, canola oil, marine oils, fish oils, algal oils, borage oil, cottonseed oil, fungal oils, interesterified oils, transesterified oils, structured lipids, or combinations of two or more thereof.

17. The method of claim 16, wherein the fat comprises omega-3 fatty acid selected from the group consisting of eicosapentaenoic acid, docosahexaenoic acid, arachidonic acid, and alpha-linolenic acid, and combinations of two or more thereof.

18. The method of claim 10, wherein the nutritional composition is administered in the form of a powder.

19. The method of claim 10, wherein the nutritional composition is administered in the form of a liquid.

20. The method of claim 10, wherein the nutritional composition comprises protein, carbohydrate, fat, and one or more nutrients selected from the group consisting of vitamins and minerals.

* * * * *